United States Patent
Jones et al.

(10) Patent No.: US 7,459,918 B2
(45) Date of Patent: Dec. 2, 2008

(54) IMPEDANCE MEASUREMENT SYSTEM WITH INCORPORATED INTERNAL MEASUREMENT DRIFT COMPENSATION NETWORKS

(76) Inventors: David Jones, 2b San Antonio Court, Mentone, Victoria (AU) 3192; Dirk Kupershoek, 78 Centenary Street, Seaford, Victoria (AU) 3198; Peter Leigh-Jones, 109 Gascards Lane, Gordon, Victoria (AU) 3345

( * ) Notice: Subject to any disclaimer, the term of this patent is extended or adjusted under 35 U.S.C. 154(b) by 0 days.

(21) Appl. No.: 11/224,354

(22) Filed: Sep. 9, 2005

(65) Prior Publication Data
US 2007/0057680 A1  Mar. 15, 2007

(51) Int. Cl.
*C12M 1/34* (2006.01)
*G01R 27/04* (2006.01)

(52) U.S. Cl. .................. 324/649; 324/629; 435/287.1; 435/288.4

(58) Field of Classification Search ............... 324/649, 324/629; 435/288.4, 287.1
See application file for complete search history.

(56) References Cited

U.S. PATENT DOCUMENTS

| | | | |
|---|---|---|---|
| 6,376,233 B1 * | 4/2002 | Wolf et al. | 435/288.4 |
| 6,553,318 B2 * | 4/2003 | Mansky | 702/22 |
| 6,668,230 B2 * | 12/2003 | Mansky et al. | 702/30 |
| 6,684,683 B2 * | 2/2004 | Potyrailo et al. | 73/24.06 |
| 6,824,974 B2 * | 11/2004 | Pisharody et al. | 435/4 |
| 2005/0153425 A1 * | 7/2005 | Xu et al. | 435/287.1 |

* cited by examiner

*Primary Examiner*—Andrew H. Hirshfeld
*Assistant Examiner*—John Zhu

(57) ABSTRACT

The present technology provides an Impedance Measurement System (ZMS) for measuring the complex impedance of each well of a single well or multiwell microtiter plate utilizing a novel combination of parallel impedance measurement channels, multiplexing, and reference impedance networks, allowing internal correction of impedance measurement drift, maximized measurement accuracy, and minimized system size.

28 Claims, 4 Drawing Sheets

IMPEDANCE MEASUREMENT SYSTEM WITH INCORPORATED INTERNAL MEASUREMENT DRIFT COMPENSATION NETWORKS

FIELD OF INVENTION

This technology relates to impedance measurement systems for the measurement of the impedance of each well of a microtiter plate.

BACKGROUND OF INVENTION

The present technology is novel in that it provides an impedance measurement system with massive parallelism, high temporal sampling, and a means for interconnecting multiple microtiter plate sensors to impedance measurement channels. The technology also includes a method for internal compensation of impedance measurement drift due to temperature changes or component aging.

SUMMARY OF THE INVENTION

The present technology provides an Impedance Measurement System (ZMS) for measuring the complex impedance of each well of a single well or multiwell microtiter plate. The ZMS utilizes a novel combination of parallel impedance measurement channels and the multiplexing of impedance measurement channels for interconnecting multiple microtiter plate sensors and reference impedance networks to the channels, allowing internal correction of impedance measurement drift, maximized measurement accuracy, and minimized system size. The system is self-contained, thermally controlled, provides well excitation and measurement, and allows the measurement data to be stored or communicated to an external host computer. The system can be used for impedance measurements of varying time periods, single or multiple frequencies, and various measurement rates. Additionally, the ZMS employs parallelism to obtain the required throughput at the repeatability required and incorporates novel calibration, self-check, and in-run compensation schemes as well as internal temperature control to ensure increased measurement accuracy and stabilization against thermal drift.

DESCRIPTION OF THE SPECIFIC EMBODIMENTS

Structural Components

Figure 1:
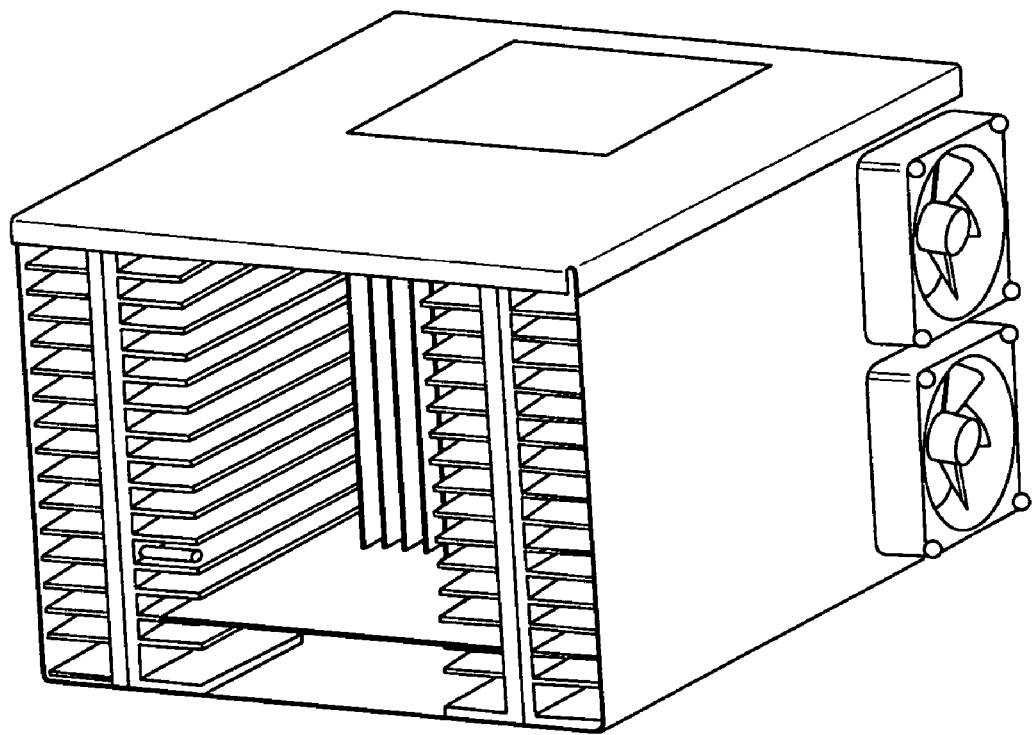
FIG. 1. ZMS General Structure
Illustration of an embodiment of the Impedance Measurement System overall structure (ZMS).

The overall system structure is displayed in FIG. 1. In one embodiment of the impedance measurement system shown in FIGS. 2 and 3, each row of sensors on a microtiter plate 10 is addressed by measurement circuitry 75 (in the form of analog signal conditioning circuits, multiplexing circuits 70, analog-digital converters, and digital signal processors) on a single daughter board 4. The interconnection of each sensor 90 from a particular well in a particular row of the microtiter plate 10 to the associated daughter board 4 is made through a Top Contact printed circuit board assembly (PCBA) 30, which carries all sensor 90 signals. Each daughter board 4 has multiplexing circuitry 70 allowing one or more measurement channels to address the sensors 90 for each well in the row.

In one embodiment, the PCBA 30 is a contact printed circuit board assembly created through the deposition of conductive inks or epoxies to form conductive traces directly on the insulating substrate of the PCBA. Conductive inks containing silver, gold, platinum, and/or carbon particles (such as those from companies such as Dupont and Acheson) are typical of those used for this purpose. Alternate circuit board embodiments utilize PCBAs created through photoengraving (which utilize a photomask and chemical etching to remove the insulator from the substrate) or PCB milling (which utilizes a mechanical milling system to mill away the insulator from the substrate).

Within the Impedance Measurement System the top contact PCBA 30 lies in a plane parallel to and immediately below the microtiter plate 10, while the daughter boards 4 are perpendicular to the plane of the microtiter plate 10. A horizontal mother board 40 is located below the daughter boards 4.

A cell plate contact array 50 provides the electrical connection between the top contact PCBA 30 and the microtiter plate 10 via spring loaded pins (Pogo pins ™) located on the contact array which interface with contact pads on the underside of the microtiter cell plate and the top surface of the PCBA. The contact pads are plated with a conductive metal, such as gold, silver, nickel, tin, or copper.

The top contact board 30, provides the connection between the daughter boards 4 and the microtiter plate sensors, as well as acting as a fluid barrier protecting the ZMS system from cell plate spills. The top contact board 30 is sufficiently thick to provide structural support against the contact forces generated by the spring contact pins of the cell plate contact array. In one embodiment, the thickness of the PCBA is in the range of 2 mm to 5 mm. In another embodiment, the PCBA thickness is in the range of 3 mm to 4 mm. In yet another embodiment, the PCBA thickness is around 3.2 mm. Additionally, the PCBA may contain an electromagnetic compatibility (EMC) screening function and an internal ground plane.

The top contact PCBA 30 contains current sensing resistors for each sensor 90. The function of these resistors is to convert the current flowing through each sensor 90 into a voltage for further signal processing. This signal is referred to as the sensor current signal. The top contact board 30 is interfaced to the daughter boards 4 via a "five wire" interface 60 or Kelvin connections to reduce measurement errors.

The daughter boards 4 carry the electronic components to drive and process a row of wells. One daughter board 4 is assigned to each row of the microtiter plate 10. In one embodiment, the top edge of the daughter boards 4 is equipped with a row of well drivers and an interlaced set of multiplexing field effect transistors 70 (or FETs, a type of transistor commonly used for signal switching or amplification, or more generally, the multiplexing circuitry for this embodiment) for well selection within a row. Positioning the FETs at the top of the daughter board 4 provides for short and uniform connection paths, with insignificant impedance, to the well electrodes via the top contact 30 and cell plate contact array 50. Further down the board, a programmable amplifier may be positioned to provide an adjustable gain for the current (I) channel, ensuring that analog to digital conversion is not subject to significant bit loss. A digital-to-analog converter may be used to provide DC offset correction to the current channel to ensure the analog-to-digital converter input is centered on the common mode range. Additionally, the daughter boards may be equipped with multiple analog-to-digital converters (including one for the voltage channel and one for the current channel), digital control circuitry (e.g., digital signal processors, memory devices, field programmable gate arrays, and/or electrically programmable logic devices), and voltage regulation circuitry. In one embodiment, these additional components are arranged below and to the side of the analog sections (as displayed by elements 75, 76, 77, and 78 in FIG. 3). The impedance data for a microtiter plate row is processed by a digital signal processor dedicated to each row and located on the daughter boards 4.

Figure 4:
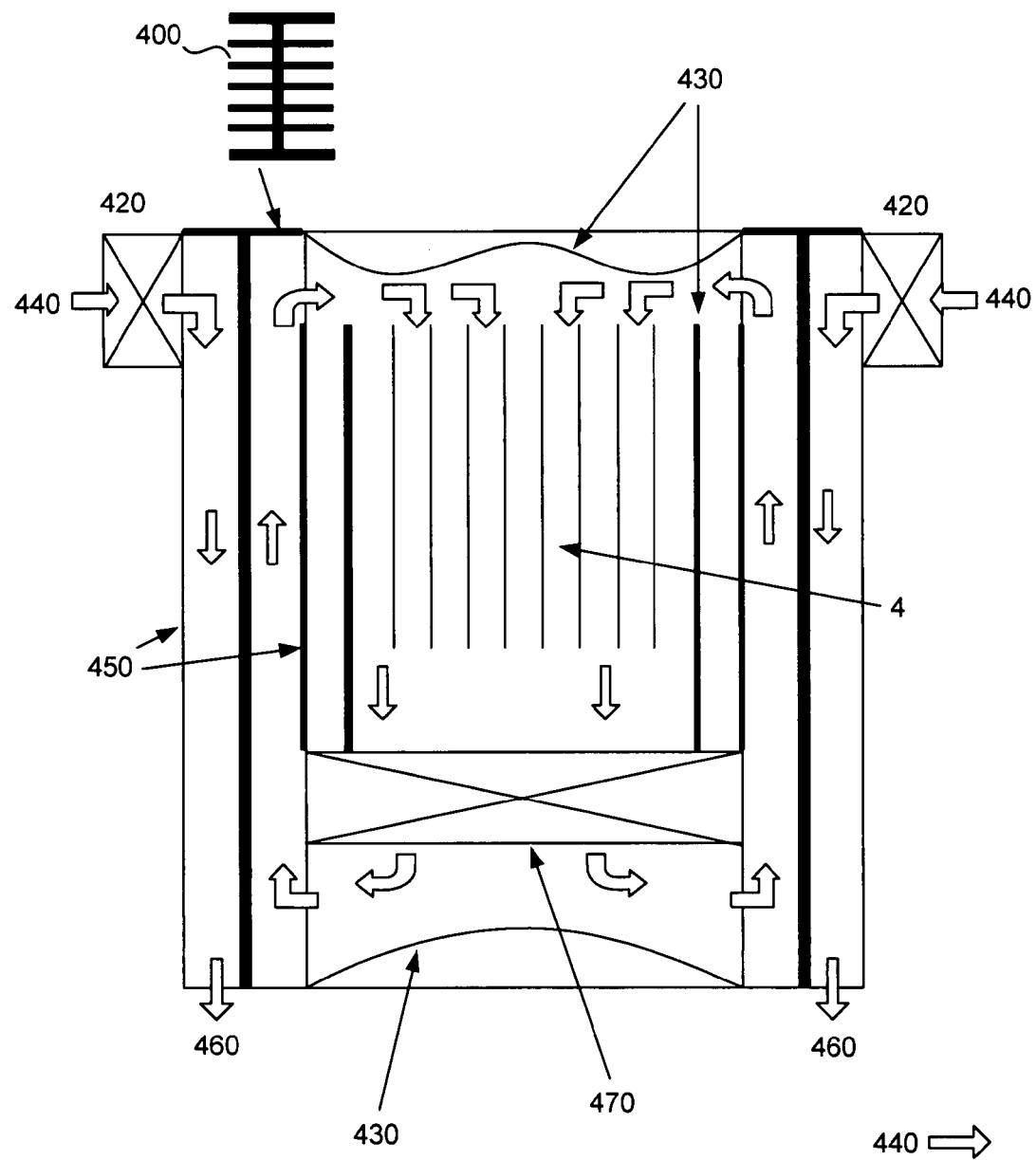
FIG. 4. Thermal Control Scheme Illustration of an embodiment of the thermal control scheme for the Impedance Measurement System (ZMS).

The ZMS may also contain deflector boards (element 430 in FIG. 4) for thermal uniformity. The deflector boards ensure that the air flow and local heating environment for the outer ZMS daughter boards 4 is similar to that for the inner boards. In one embodiment, the deflector boards 430 have local heat sources added to assist in the thermal control. In an additional embodiment, the heat source is located behind the deflector boards on a separate deflector. The deflector boards 430 also provide physical support the for the ZMS board stack. The deflector boards 430 have the same connector arrangement as the daughter boards 4 but have additional mounting brackets which are screwed to the deflector boards 430 and mother board 40 (and additionally, may be screwed to the PCBA, or top contact board 30).

The ZMS daughter boards 4 mate at their lowest edge with the mother board 40. The mother board 40 accommodates various electrical components and functions, including the digital signal source 42 excitation low pass filtering, supervisory processing, ROM/RAM, host data communications, and may control enclosure temperature. The mother board processes the impedance measurement data (via element 44 of FIG. 3.), at a specific time and frequency, of all wells of the microtiter plate 10 and communicates the results to the system controller.

Electrical performance dictates that the daughter board assembly 4 be closely coupled to the top contact board 30 and that the circuitry be kept as tightly arranged as possible. The top contact board 30 must be maintained in an accurate physical relationship with the contact array 50 and is the reference point for the board assembly. The top contact board 30 and the top contact array 50 are aligned by means of locating features to positioning bars on the top plate.

The top contact board 30 supported peripherally by a top plate. A combined fluid seal and electromagnetic compatibility gasket is used between the board and plate. In one embodiment, the full board stack is suspended from the PCBA board 30 via the deflector boards 430 which provide a mechanical connection between the top contact board 30 and the mother board 40, eliminating the need for any mechanical supports from the base or side of the ZMS structure and eliminating the differential thermal expansion problems with board to board connections. The main ZMS chassis is created by a "U" shaped folded outer shell surrounding the thermal control heat exchanger extrusions and providing baffles 450 that control both the internal and external air flow 440. The top plate, front and rear covers are made of sheet steel in one embodiment. In additional embodiments, these structures can be made from any combination of case, sheet milled steel, aluminum, or stainless steel.

This physical arrangement and electrical configuration maximizes the accuracy of the impedance measurements by minimizing the electrical path length and stray impedances associated with connecting the microtiter plate sensor to the measurement circuit. The minimized path length also optimizes phase and gain tracking, and maximizes the immunity to noise.

The physical configuration minimizes the number of needed mechanical supports and eliminates key thermal expansion problems associated with other designs. The configuration minimizes the size of the Impedance Measurement System thereby allowing more efficient internal packaging and thermal stabilization of the electronic components (due to reduced convection). The minimized path length also optimizes phase and gain tracking, and maximizes the immunity to noise.

In an additional embodiment, each column of sensors, rather than each row of sensors, on a microtiter plate is addressed by measurement circuitry on a single daughter board with the system arrangement of the boards remaining the same.

Functional Elements

For each impedance datum in the domain (characterized by well number, frequency, and time), each well is excited with a sinusoidally-varying voltage wave, and the resultant voltage across and current through the well are measured. At a particular point in time, all wells on the plate are excited by sine waves of the same frequency and phase to minimize well interaction and the risk of intermodulation (the "multiplication" or amplification of one frequency in a nonlinear element of a system by other frequencies transmitted through the system).

Digitally Generated "Sine Wave" Signal Source

The sine wave excitation signal is produced by a high speed direct digital synthesizer located on the mother board. In one embodiment, the synthesizer runs at a clock frequency of 256 MHz. Alternate frequencies include any frequency from 50 MHz to 400 MHz, with appropriate filtering and a compatible synthesizer device. At high frequencies, the number of points per cycle is reduced, where the number of points is dictated by the ratio of master clock and drive frequencies; higher clock frequencies are desirable.

Sine Low Pass Filters

The digitally generated since wave is low pass filtered to reduce the stair step (the sudden increases in amplitude) resulting from time step limiting at high frequencies and any amplitude resolution limiting at lower frequencies. The low pass filtering occurs on the mother board and is accomplished with three filter groups each covering one third (on a log scale) of the frequency range. The choice of filter bank in use at a given point in time is selected by amplifiers with output disable (high impedance, Z) capability. Four cascaded first order stages are used in each filter group. This approach has been selected to provide maximum stability and minimum settling time. Each filter group has less than 6 db fall off in output at the high end of its frequency range but provides 40 db attenuation for the lowest stair step frequency component in the digitized sine wave, the result being a very clean, and agile sine source.

Well Driver/Buffer Array

The output of the direct digital synthesizer (DDS) filter group is buffered by a driver array. A master buffer drives a set of row drivers (one per Daughter board). The row drivers each drive a set of individual well drivers (sixteen per daughter board). Each well drive is a short circuit proof, low impedance, fixed output, voltage source. This approach isolates each well and permits the drive signal to be closely coupled to the well, thereby avoiding the phase shifts that would be incurred had long drive cables been used. Drive current is limited to 100 mA root mean square (RMS). Drive voltage has an upper limit of 2 volts peak to peak. Actual well drive will be of the order of 100 mV peak to peak to maximize signal levels without introducing significant distortion.

Excitation

Each well is subject to a stepped sweep (a series of single frequency bursts-one burst for each selected frequency). The bursts consist of an integral number of cycles. In one embodiment, the number of cycles is typically 15. The number of cycles for additional embodiments are chosen to be sufficient for well and gain multiplexer switching transients to settle and to obtain the necessary number of sample points. From preliminary modeling and testing, no more than 68.2 ms per well for all frequencies is required to obtain sufficient samples. For an embodiment in which a 96 well plate with 12 wells per row plus four reference network channels, calculations to determine sufficient samples suggest a 1091 mS measurement period, leaving 409 mS for multiplexer switching and signal settling within the target 1.5 second update period.

Programmable Current Gain Stage with Offset Adjustment

The programmable current gain stage provides gain in multiples of two from 1 through 64. The gain bandwidth of this stage is matched to the frequency range. Gain selection is via a multiplexer in the feedback path of the cascaded gain stages in the current path. The gain multiplexer is replicated in the voltage path to preserve the optimum phase tracking. Residual phase and gain errors are reduced by linear correction techniques within the digital signal processor from the scan to scan measurements of the reference resistance/capacitance networks. Offset adjustment is accomplished by injecting a current into the stage summing node. This current is produced by a digital to analog converter under software control to ensure the signal presented to the analog to digital converter ADC is centered about the AC common mode voltage. The significance of offset adjustment requirements has been reduced through the adoption of higher current sense "shunt" resistance value.

The gain/phase and DC offset compensation provides an "adjustment free" design which corrects for component to component variation as well as any drift in components.

High Speed Clipper

During gain switching and well selection, transients are generated even though zero crossing voltage points are selected. The amplitude of these transients is clipped by high speed limiting amplifiers to ensure the analog to digital converters are not taken outside their linear input limits.

Differential Analog to Digital Converter Drivers

A buffer/differential driver provides complimentary signals centered about the analog to digital converter common mode voltage.

Analog to Digital Converters

A high speed, high resolution ADC is used for each of the current and the voltage channels. The ADCs are 14 bit, 60 Mega Samples per second to provide high speed and accuracy (especially at the lower current values anticipated in some circumstances). To ensure the lowest drift the ADC's will operate at constant high clock rate with excess samples then being discarded by the field programmable gate array FPGA or electrically programmable logic device EPLD. An FPGA or EPLD is used on both mother and daughter boards to perform general housekeeping duties and also specific high speed functions related to excitation frequency generation and data acquisition.

The current through and the voltage across each well is scaled, converted to digital values, and transmitted via the measurement channels to either a storage device or an associated computer. Careful matching of both signal levels and topology of the current and voltage channels ensures excellent phase-tracking especially at high frequencies. On board calibration channels are referenced to minimize residual gain and phase errors.

Data and Control Interface

An embedded instrument control computer is the external interface for data and control for the ZMS. The interface must be able to accommodate and expected data rate of approximately 5000 data points per second. In one embodiment, this serial link is provided by a USB 1.1 The USB would also support a possible interface directly between the ZMS and an external computer. Alternative interfaces include ethernet, USB, RS-485, or Firewre.

Internal Calibration

The ZMS provides for calibration, self-check, in-run compensation, and drift compensation.

Calibration of the unit is performed by measuring precision, calibration resistor networks on a "calibration plate" and correcting the internal reference networks.

Self-checking is performed by exercising the ZMS over a defined frequency set on the internal reference networks and comparing results with the stored factory calibration values. For self-tests, the ZMS performs a stepped sweep on all reference RC networks without any calibration factors applied. The results are compared with a set of values downloaded from the instrument computer. The stored values are established at the time of manufacture. The results returned from the sweep must lie within the bounds set by the stored values.

In-run auto compensation is performed by including high stability RC networks as reference channels which are treated as an additional well and applying compensation derived from the reference data set to the well data set. For in-run compensation, three precision RC networks are included in the system. In one embodiment, three precision RC networks are included. An alternative embodiment includes four reference networks. Additional embodiments may include any number greater than three. The principal reference network has values set to match the gross characteristics of a well with cells. The other networks have values that provide an impedance characteristic both above and below the primary network to allow checking and compensation for system non-linearity. These networks are also used with the self-checking feature of the ZMS.

Drift compensation is achieved by performing a stepped sweep on the calibration networks and the wells at the start of each run to determine the DC basic offset, gain, and phase correction factors required for each frequency and current gain setting. During the per row scan interval, the ZMS performs a stepped sweep on the reference RC networks. Any changes from the values obtained form the start of run values is used to determine drift compensation that is applied to the well results. The compensation factors required to bring the calibration networks to their start of run value are applied to the well results, greatly reducing temperature effects and other possible drift effects including aging and component to component variation. The stability and precision over any run is primarily determined by the reference RC networks.

Thermal Control

In addition to the temperature compensation provided by the self calibration and in-run calibration networks, the ZMS requires a stable controlled thermal environment. To achieve the desired rate of ZMS accuracy and repeatability, temperature control to within ±1.5° C. is necessary. In an additional embodiment, the temperature control must be within ±1.0° C. In yet a further embodiment, the temperature control must be within ±0.5° C.

The ZMS thermal control system includes a high flow rate, forced air circulation system to provide spatial temperature uniformity ability to remove waste heat generated by ZMS heating to maintain optimum operating temperature monitoring of gross air temperature and gradients a heat exchanger to prevent build-up of contaminants causing surface leakage currents The ZMS thermal control system maintains very high linear air velocities over the daughter boards to keep amplifier devices to reasonable temperatures, to reduce noise, and to improve component reliability. The thermal control system achieves this using a two part scheme. A sealed inner air volume around the ZMS circuit boards recirculates air at high speed between boards and an inner heat exchanger surface. The heat generated is then removed by external fans blowing air at ambient temperature across the outer heat exchanger surface. The control scheme uses coarse control of the external fan speed to compensate for changes in ambient air temperature as an open loop control. Accurate internal air temperature is maintained by adding heat with a heater (or heaters) mounted on the heat exchangers or another internal surface. This is a precise closed loop linear control. The temperature control element for the ZMS may be located either within the ZMS itself or external to the system.

Figure 2:
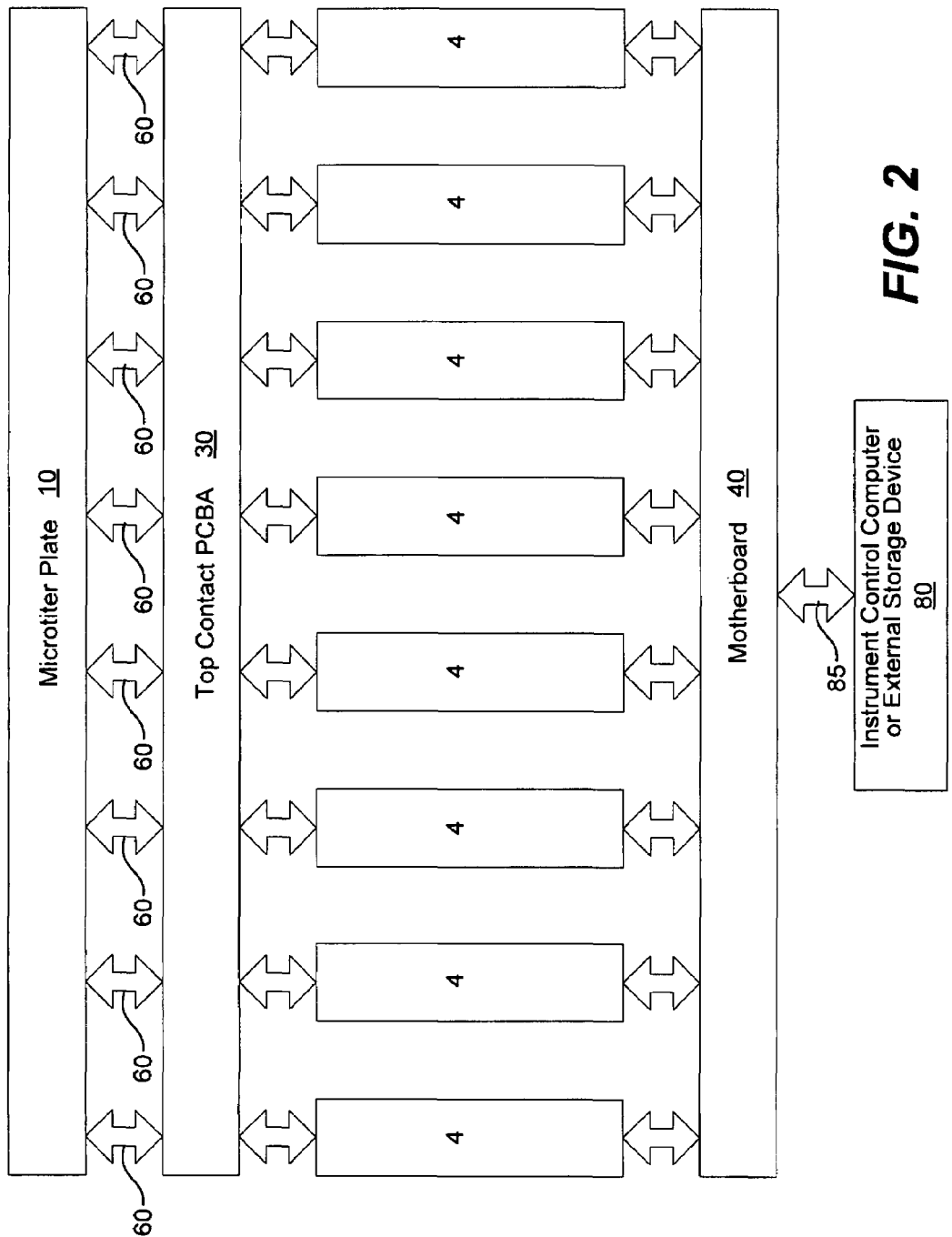
FIG. 2. Impedance Measurement System Component Structure Illustration of an embodiment of the main components of the Impedance Measurement System (ZMS) and their relationships to each other.
Figure 3:
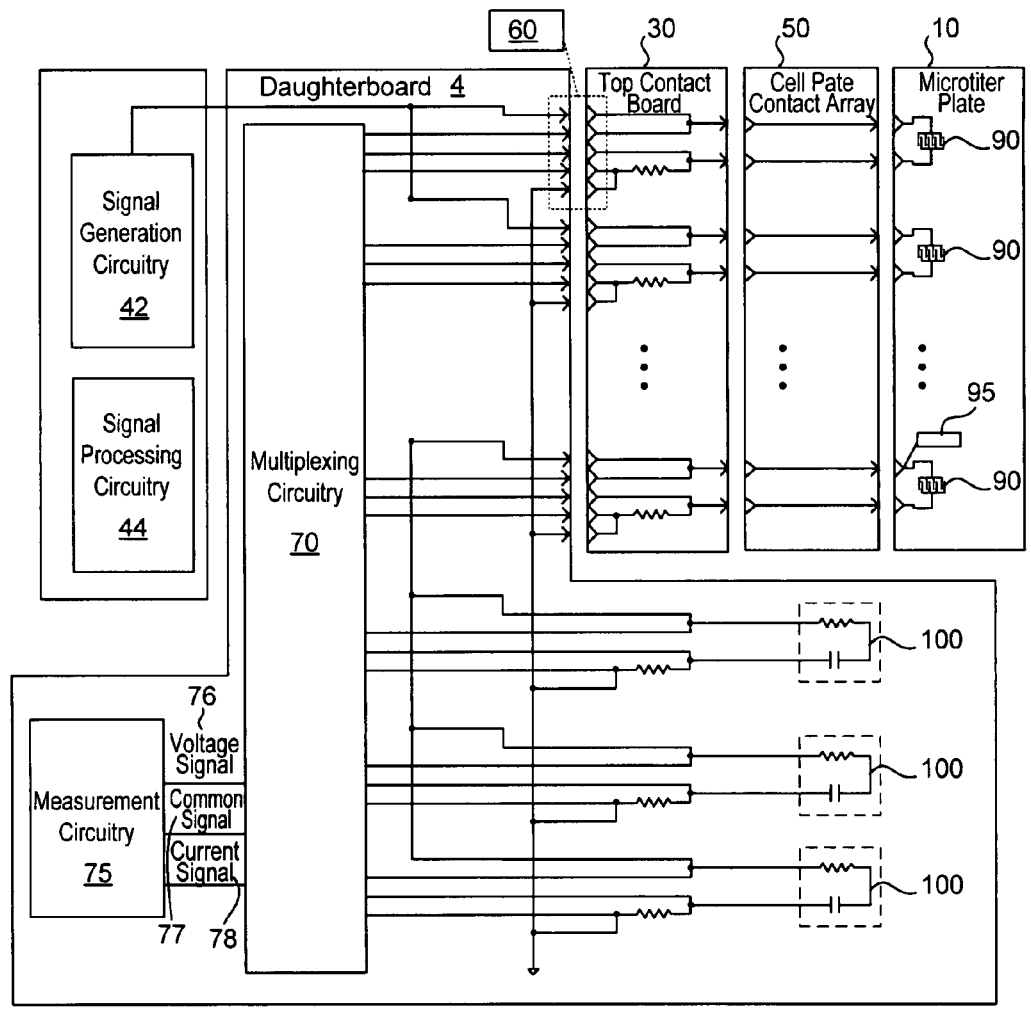
FIG. 3. Impedance Measurement System Circuitry Schematic Illustration of an embodiment of the circuitry of the Impedance Measurement System (ZMS).

The ZMS thermal control system is displayed in FIG. 2. In a representative embodiment, a variable speed fan 420 pulls air 440 past the baffles 450 and heat sinks 400, exiting to the rear of the system 460. Interior to the system, airflow 440 passes a system of baffles 450, is deflected 430 onto the ZMS daughter boards 4, and the moves past a high-flow, speed monitored fan 470. Deflectors 430 then direct the air flow 440 back towards the baffles 450.

SUMMARY

While the above is a complete description of possible embodiments of the device, various alternatives, modifications, and equivalents may be used. The above description should be viewed as only exemplary embodiments of the device, the boundaries of which are appropriately defined by the metes and bounds of the following claims.

What is claimed is:

1. An impedance measurement system for measuring the complex impedance of each well of a microtiter plate, the microtiter plate wells being formed in an array of rows and columns, the microtiter plate having a topside and an underside, the microtiter plate comprising sensors in the well bottoms and contact pads on the underside of the microtiter plate, the impedance measurement system comprising:

(1) at least one daughter board comprising measurement and multiplexing circuitry, each daughter board being associated with a particular row of wells on the microtiter plate, the at least one daughter board lying in a plane perpendicular to the plane of the microtiter plate;

(2) at least one top contact board, each top contact board assembly providing an interconnection means between a sensor associated with a particular well in a particular row and the daughter board associated with the row, the at least one top contact board lying in a plane which is parallel to the plane of the microtiter plate, above the at least one daughter board, and below the microtiter plate;

(3) a motherboard comprising signal generation and signal processing circuitry, the mother board lying in a plane which is parallel to the plane of the microtiter plate and below the at least one daughter board;

(4) a cell plate contact array providing a means for electrical connection between the at least one printed circuit board assembly and the microtiter plate contact pads;

(5) a means for thermal control; and (6) a means for system impedance drift compensation comprising at least three resistor-capacitor networks.

2. The impedance measurement system of claim 1, wherein the microtiter plate has 96 wells arranged in an array of 8 rows and 12 columns.

3. The impedance measurement system of claim 1, wherein the at least one top contact board is a contact printed circuit board assembly.

4. The impedance measurement system of claim 1, wherein the at least one printed top contact board has a thickness above 3 mm and less than 4 mm.

5. The impedance measurement system of claim 1, wherein the at least one printed circuit board assembly interfaces with the at least one daughter board via a five wire.

6. The impedance measurement system of claim 1, wherein the means for thermal control comprises deflector boards and at least one heat source.

7. The impedance measurement system of claim 1 wherein the means for thermal control is able to control the system temperature to within ±1.5° C.

8. The impedance measurement system of claim 1 wherein the means for thermal control is able to control the system temperature to within ±1.0° C.

9. The impedance measurement system of claim 1, wherein the means for system impedance drift compensation comprises four resistor-capacitor networks.

10. The impedance measurement system of claim 9, wherein the three resistor-capacitor networks comprise a reference network with impedance values equivalent to a microtiter well sensor with cells, an R-C network with impedance characteristics above the reference network, and an R-C network with impedance characteristics below the reference network.

11. The impedance measurement system of claim 1 additionally comprising an external interface means for data access and system control.

12. The impedance measurement system of claim 11, wherein the external interface means is an instrument control computer.

13. The impedance measurement system of claim 11, wherein the external interface means is an external storage device.

14. The impedance measurement system of claim 11, wherein the external interface means interfaces with the impedance measurement system via a USB serial cable.

15. An impedance measurement system for measuring the complex impedance of each well of a microtiter plate, the microtiter plate wells being formed in an array of rows and columns, the microtiter plate having a topside and an underside, the microtiter plate comprising contact pads on the underside of the microtiter plate, the impedance measurement system comprising:
(1) at least one daughter board comprising measurement and multiplexing circuitry,
each daughter board being associated with a particular row of wells on the microtiter plate,
the at least one daughter board lying in a plane perpendicular to the plane of the microtiter plate;
(2) at least one top contact board assembly,
each top contact board assembly providing an interconnection means between a sensor associated with a particular well in a particular column and the daughter board associated with the column,
the at least one top contact board lying in a plane which is parallel to the plane of the microtiter plate, above the at least one daughter board, and below the microtiter plate;
(3) a motherboard comprising signal generation and signal processing circuitry,
the mother board lying in a plane which is parallel to the plane of the microtiter plate and below the at least one daughter board;
(4) a cell plate contact array providing a means for electrical connection between the at least one printed circuit board assembly and the microtiter plate contact pads;
(5) a means for thermal control; and
(6) a means for system impedance measurement drift compensation comprising at least three resistor-capacitor networks.

16. The impedance measurement system of claim 15, wherein the microtiter plate has 96 wells arranged in an array of 8 rows and 12 columns.

17. The impedance measurement system of claim 15, wherein the at least one top contact board assembly is a contact printed circuit board assembly.

18. The impedance measurement system of claim 15, wherein the at least one printed circuit board assembly has a thickness above 3 mm and less than 4 mm.

19. The impedance measurement system of claim 15, wherein the at least one printed circuit board assembly interfaces with the at least one daughter board via a five wire.

20. The impedance measurement system of claim 15, wherein the means for thermal control comprises deflector boards and at least one heat source.

21. The impedance measurement system of claim 15 wherein the means for thermal control is able to control the system temperature to within ±1.5° C.

22. The impedance measurement system of claim 15 wherein the means for thermal control is able to control the system temperature to within ±1.0° C.

23. The impedance measurement system of claim 15, wherein the means for system impedance measurement drift compensation comprises three resistor-capacitor networks.

24. The impedance measurement system of claim 23, wherein the three resistor-capacitor networks comprise (1) a reference R-C network with impedance values equivalent to a microtiter well with cells, (2) an R-C network with impedance characteristics above the impedance values of the reference R-C network, and (3) an R-C network with impedance characteristics below the impedance values of the reference R-C network.

25. The impedance measurement system of claim 15 additionally comprising an external interface means for data access and system control.

26. The impedance measurement system of claim 25, wherein the external interface means is an instrument control computer.

27. The impedance measurement system of claim 25, wherein the external interface means is an external storage device.

28. The impedance measurement system of claim 25, wherein the external interface means interfaces with the impedance measurement system via a USB serial cable.

* * * * *

UNITED STATES PATENT AND TRADEMARK OFFICE
CERTIFICATE OF CORRECTION

PATENT NO. : 7,459,918 B2 Page 1 of 1
APPLICATION NO. : 11/224354
DATED : December 2, 2008
INVENTOR(S) : Jones et al.

It is certified that error appears in the above-identified patent and that said Letters Patent is hereby corrected as shown below:

In line 10 of claim 15 (column 9, line 6) change "row" to --column--.

Signed and Sealed this

Eleventh Day of May, 2010

David J. Kappos
*Director of the United States Patent and Trademark Office*